(12) United States Patent
Sonntag et al.

(10) Patent No.: US 11,957,457 B2
(45) Date of Patent: Apr. 16, 2024

(54) SYSTEM AND METHOD FOR POSTURE AND MOVEMENT REGULATION

(71) Applicant: ADDASENSE HEALTH GMBH, Unterhaching (DE)

(72) Inventors: Peter Sonntag, Munich (DE); Stephan Bollinger, Munich (DE)

(73) Assignee: ADDASENSE HEALTH GMBH, Unterhaching (DE)

( * ) Notice: Subject to any disclaimer, the term of this patent is extended or adjusted under 35 U.S.C. 154(b) by 972 days.

(21) Appl. No.: 16/323,175

(22) PCT Filed: Aug. 3, 2017

(86) PCT No.: PCT/EP2017/069598
§ 371 (c)(1),
(2) Date: Feb. 4, 2019

(87) PCT Pub. No.: WO2018/029064
PCT Pub. Date: Feb. 15, 2018

(65) Prior Publication Data
US 2019/0175073 A1 Jun. 13, 2019

(30) Foreign Application Priority Data
Aug. 9, 2016 (DE) .......................... 102016114766.4

(51) Int. Cl.
*A61B 5/11* (2006.01)
*A61B 5/00* (2006.01)
(Continued)

(52) U.S. Cl.
CPC .......... *A61B 5/1116* (2013.01); *A61B 5/1071* (2013.01); *A61B 5/1101* (2013.01);
(Continued)

(58) Field of Classification Search
CPC ..... A63B 23/0244; A61B 5/11; A61B 5/1116; A61B 5/1121; A61B 5/1122; A61B 5/1126; A61B 5/74–7415
See application file for complete search history.

(56) References Cited

U.S. PATENT DOCUMENTS

| 4,730,625 A | 3/1988 | Fraser et al. ................... 600/594 |
| 2004/0116815 A1* | 6/2004 | Yang .................... A61B 5/7405 |
| | | 600/485 |

(Continued)

FOREIGN PATENT DOCUMENTS

| CN | 102973274 A | 3/2013 | ............... A61B 5/11 |
| CN | 104524742 A | 4/2015 | ............... A61B 5/11 |

(Continued)

OTHER PUBLICATIONS

Nichols, Deborah S. "Balance retraining after stroke using force platform biofeedback." Physical therapy 77.5 (1997): 553-558. (Year: 1997).*

(Continued)

*Primary Examiner* — David J. McCrosky
(74) *Attorney, Agent, or Firm* — Bodner & Bodner, PLLC; Gerald T. Bodner; Christian P. Bodner

(57) ABSTRACT

A system for posture and movement regulation includes at least one body-position sensor unit, at least one arithmetic unit, and at least one output unit for outputting an acoustic signal, and/or at least one output unit for outputting a vibration signal.

9 Claims, 15 Drawing Sheets

Figure 1A:
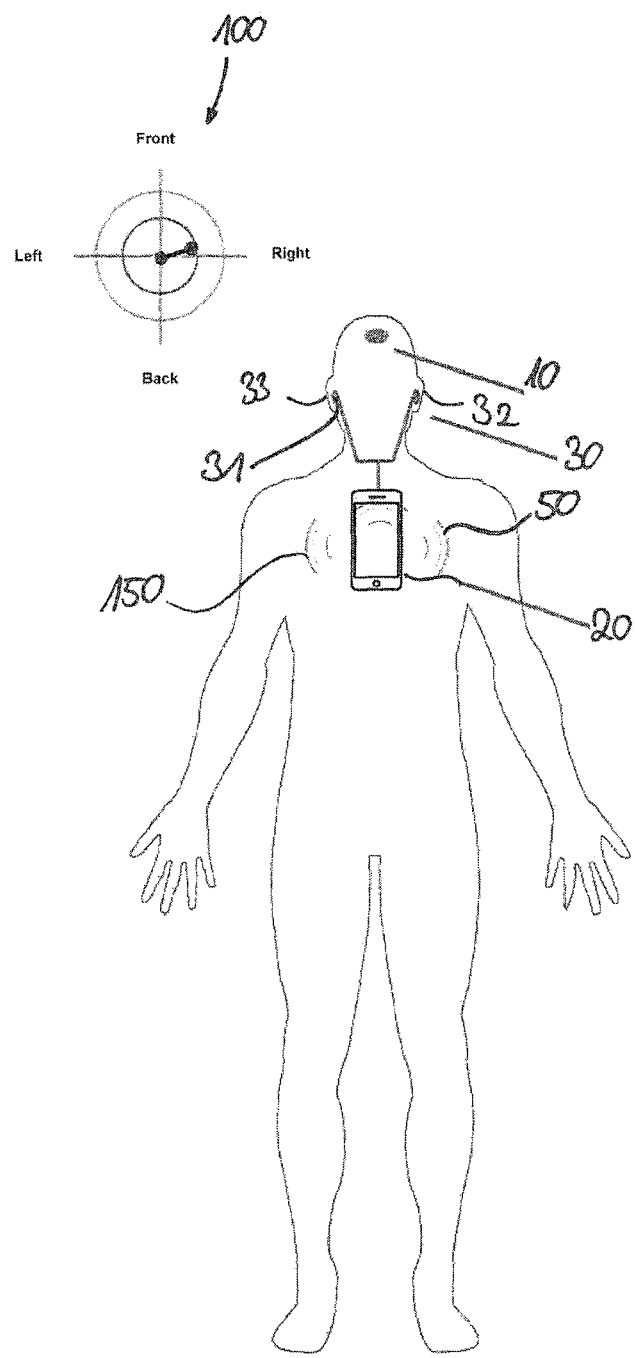

(51) Int. Cl.
*A61B 5/107* (2006.01)
*A61B 5/375* (2021.01)

(52) U.S. Cl.
CPC ............ *A61B 5/112* (2013.01); *A61B 5/1121* (2013.01); *A61B 5/6804* (2013.01); *A61B 5/6898* (2013.01); *A61B 5/7405* (2013.01); *A61B 5/742* (2013.01); *A61B 5/7455* (2013.01); *A61B 5/746* (2013.01); *A61B 5/0022* (2013.01); *A61B 5/375* (2021.01); *A61B 5/6805* (2013.01); *A61B 5/6823* (2013.01); *A61B 5/683* (2013.01); *A61B 5/6831* (2013.01); *A61B 2505/09* (2013.01); *A61B 2560/0223* (2013.01); *A61B 2562/0219* (2013.01)

(56) References Cited

U.S. PATENT DOCUMENTS

| | | | | |
|---|---|---|---|---|
| 2007/0015611 | A1* | 1/2007 | Noble | A61B 5/1126 473/450 |
| 2007/0249466 | A1 | 10/2007 | Chiari et al. | 482/1 |
| 2014/0029767 | A1 | 1/2014 | Jarvinen et al. | 381/119 |
| 2014/0330172 | A1 | 11/2014 | Jovanov et al. | 600/595 |
| 2015/0065919 | A1 | 3/2015 | Cuevas et al. | 600/587 |
| 2016/0045386 | A1* | 2/2016 | Sandler | A61B 5/742 623/24 |
| 2017/0215769 | A1* | 8/2017 | Lu | A61B 5/1116 |

FOREIGN PATENT DOCUMENTS

| | | | | |
|---|---|---|---|---|
| CN | 105380652 | A | 3/2016 | ............ A61B 5/103 |
| DE | 19911612 | A1 | 10/2000 | ............ A61B 5/11 |
| DE | 10304238 | A1 | 8/2004 | ............ A61B 5/11 |
| DE | 202005015889 | U1 | 1/2006 | ............ A41D 27/00 |
| DE | 102010003871 | A1 | 10/2011 | ............ A61B 5/11 |
| DE | 202014101266 | U1 | 4/2014 | ............ A61B 5/107 |
| EP | 1761167 | A1 | 3/2007 | ............ A61B 5/00 |
| KR | 101226195 | B1 * | 1/2013 | |
| WO | WO2004066837 | A1 | 8/2004 | ............ A61B 5/11 |
| WO | WO2006005978 | A1 | 1/2006 | ............ A61B 5/00 |
| WO | WO2016055848 | A1 | 4/2016 | ............ A61B 5/11 |

OTHER PUBLICATIONS

Z. Matjacic et al, "Arm-free paraplegic standing. II. Experimental results," in IEEE Transactions on Rehabilitation Engineering, vol. 6, No. 2, pp. 139-150, Jun. 1998, doi: 10.1109/86.681179. (Year: 1998).*

Rapoport, B., "Essence Reveals the History of Sterophonic Sound" essenceelectrostatic.com. Aug. 15, 2014. https://web.archive.org/web/20150415220931/https://www.essenceelectrostatic.com/essence-reveals-history-stereophonic-sound/ (Year: 2014).*

Machine translation of KR 101226195 B1 (Year: 2013).*

The Notification Concerning Transmittal of International Preliminary Report on Patentability (Chapter I of the Patent Cooperation Treaty), in English, dated Feb. 21, 2019, which was issued by the International Bureau of WIPO in Applicant's corresponding international PCT application having Serial No. PCT/EP2017/069598, filed on Aug. 3, 2017.

The English translation of the International Preliminary Report on Patentability (Chapter I of the Patent Cooperation Treaty), dated Feb. 12, 2019, which was issued by the International Bureau of WIPO in Applicant's corresponding international PCT application having Serial No. PCT/EP2017/069598, filed on Aug. 3, 2017.

The Written Opinion of the International Searching Authority, in English, dated Nov. 2, 2017, which was issued by the International Bureau of WIPO in Applicant's corresponding international PCT application having Serial No. PCT/EP2017/069598, filed on Aug. 3, 2017.

The International Search Report, in English, dated Nov. 2, 2017, which was issued by the International Bureau of WIPO in Applicant's corresponding international PCT application having Serial No. PCT/EP2017/069598, filed on Aug. 3, 2017.

An Office Action (in German), dated Jun. 24, 2022, issued by the European Patent Office for Applicant's related European Patent Application No. 17749691.6.

An Office Action (in Chinese), dated Feb. 8, 2022, issued by the CHina National Intellectual Property Administration for Applicant's related Chinese Patent Application No. CN201780060319.5.

An Office Action (in Chinese), dated May 25, 2021, issued by the China National Intellectual Property Administration for Applicant's related Chinese Patent Application No. CN201780060319.5.

* cited by examiner

SYSTEM AND METHOD FOR POSTURE AND MOVEMENT REGULATION

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

Not Applicable

STATEMENT REGARDING PRIOR DISCLOSURES BY THE INVENTOR OR A JOINT INVENTOR

Not Applicable

BACKGROUND OF THE INVENTION

(1) Field of the Invention

The invention relates to a system and method for posture and movement regulation. Furthermore, the invention relates to a method for posture and movement regulation for humans, in particular by using a system according to the invention. Moreover, the invention relates to a computer readable storage medium.

(2) Description of Related Art

Persons who suffer from walking disorders and/or balance disorders and/or postural disorders, or who are restricted in their mobility due to operations, are usually very insecure during walking. These persons often adopt protective postures. This may intensify postural damage.

BRIEF SUMMARY OF THE INVENTION

It is the task of the present invention to specify a system for posture and movement regulation so that at least the group of persons described above regains more safety when walking or moving. The system is intended to help prevent accidents involving persons with an unstable gait. Additional safety is to be provided for persons with an impaired sense of balance. In particular, protective postures and an antalgic gait as well as incorrect and unhealthy movements or sequences of movements are to be avoided. Moreover, in the event of only one-sided body posture damage and/or gait disorders, the system for body posture and movement regulation should make it possible to act specifically on this one-sided disorder.

Furthermore, the system should make it possible to consciously and correctly carry out training sessions in case of changes in position, rotation, and posture of bodies or individual body parts to be trained. The system should serve as a training means, for example, to improve joint mobility or to improve mobility in the event of muscle shortening or weakness in individual limbs or in case of movement restrictions in individual limbs or groups of limbs. Therapy goals with a therapist should be accelerated, simplified or intensified by applying the inventive system.

Moreover, it is the task of the present invention to specify a method for posture and movement regulation for humans. The method should preferably be performable with the system according to the invention.

The task of the invention is accomplished by a system for posture and movement regulation in accordance with the teachings set forth herein. Furthermore, the task of the invention is accomplished by a method for posture and movement regulation in accordance with the teachings set forth herein. Moreover, the task of the invention is accomplished by a computer readable storage medium in accordance with the teachings set forth herein.

The dependent claims represent at least appropriate configurations and further modifications of the inventive system and of the inventive method.

The inventive system for posture and movement regulation can also be described as a system for walking and movement regulation aid. Since movement regulation also comprises a regulation of walking or gait, the system is referred to in the following as a system for posture and movement regulation.

The inventive system for posture and movement regulation comprises:
- at least one position sensor, in particular at least one body position sensor unit,
- at least one arithmetic unit, and
- at least one output unit for outputting an acoustic signal and/or at least one output unit for outputting a vibration signal.

An output unit can be formed for outputting (at least) one stereo acoustic signal.

At least one output unit is provided. The system has at least one output unit for outputting an acoustic signal and/or at least one output unit for outputting a vibration signal.

The position sensor can be an acceleration sensor and/or a rotary motion sensor, in particular a rotation rate sensor. In other words, the body position sensor unit may comprise an acceleration sensor and/or a rotary motion sensor, in particular a rotation rate sensor, and/or a gravitational sensor and/or a tremor sensor and/or a magnetic sensor. It is possible for the body position sensor unit to comprise multiple position sensors. The position sensors can be formed to be identical or different.

In particular, it is possible for the body position sensor unit to comprise multiple sensors arranged at different parts of the body and/or different positions of the body.

The inventive system may also have a display unit for visually displaying the data obtained from the body position sensor unit. Furthermore, it is possible for the system to have a control unit for setting system parameters. In a particularly preferred embodiment of the invention, the control unit and the display unit can be combined in one module. This module may be what is commonly called an interface element module. The interface element module can also be called an input and output module.

The at least one position sensor, in particular the at least one body position sensor unit, and/or the at least one arithmetic unit and/or the at least one output unit for outputting an acoustic signal and/or the at least one output unit for outputting a vibration signal and/or the at least one display unit and/or the at least one control unit can be formed within a mobile communication device, in particular within a cellular phone.

Furthermore, it is possible that the at least one position sensor, in particular the at least one body position sensor unit, and/or the at least one arithmetic unit and/or the at least one output unit for outputting an acoustic signal and/or the at least one output unit for outputting a vibration signal and/or the at least one display unit and/or the at least one control unit is/are formed as part of a mobile communication device, in particular of a cellular phone.

The mobile communication device may be a cellular phone or a smartphone or a PDA or a handheld. The mobile communication device may be a device specifically formed for the inventive application. The mobile communication device preferably comprises at least one radio interface.

The mobile communication device can preferably receive and/or transmit radio signals. The radio signals may be BLUETOOTH short-range wireless communication technology standard signals and/or infrared signals and/or 3G signals and/or 4G signals and/or LTE signals and/or UMTS signals and/or WLAN signals.

Preferably, wireless data transmission is possible with the help of the mobile communication device. The wireless data transmission can be formed between the body position sensor unit and the arithmetic unit and/or between the arithmetic unit and the output unit for outputting an acoustic signal and/or the output unit for outputting a vibration signal.

As an alternative or in addition, it is possible to form wired data transmission paths. It is possible that a cable connection is formed for the transmission of data between the body position sensor unit and the arithmetic unit and/or between the arithmetic unit and the output unit for outputting an acoustic signal and/or the output unit for outputting a vibration signal.

The at least one position sensor, in particular the at least one body position sensor unit, may be a position sensor of the mobile communication device. In other words, the data and/or signals and/or information of at least one position sensor of a mobile communication device can be picked up.

The arithmetic unit can be the arithmetic unit of the mobile communication device. Furthermore, it is possible that an arithmetic unit which is independent of the mobile communication device, in particular an external arithmetic unit, is formed.

The output unit for outputting an acoustic signal may be a headphone that is assigned to a mobile communication device or that is part of a mobile communication device. The headphone may be connected to the mobile communication device by cable. As an alternative and/or in addition, it is possible that a radio connection exists or can be established between the headphone and the mobile communication device.

The output unit for outputting (at least) one acoustic signal, in particular a stereo acoustic signal, may be a headphone or a bone conduction headphone or a radio headphone, in particular a BLUETOOTH short-range wireless communication technology standard headphone, or an in-ear headphone or an implant, in particular a cochlear implant.

The output unit for outputting a vibration signal may be a radio vibration generator, in particular a BLUETOOTH short-range wireless communication technology standard vibration generator, or a vibration generator of the/a mobile communication device.

As an alternative or in addition, it is possible that the output unit for outputting a vibration signal is formed as an output unit for outputting a stimulation current.

The system may also comprise a carrying device for the at least one position sensor, in particular for the at least one body position sensor unit, and/or the at least one output unit for outputting an acoustic signal and/or the at least one output unit for outputting a vibration signal and/or for the arithmetic unit and/or for the control unit and/or for the display unit.

The carrying device may be formed as a pouch with at least one strap. The pouch may be formed in the manner of a neck pouch. For example, a mobile communication device can be located or transported in the pouch. At least one position sensor, in particular at least one body position sensor unit and/or at least one output unit for outputting an acoustic signal and/or at least one output unit for outputting a vibration signal and/or an arithmetic unit and/or a control unit and/or a display unit can be located or transported in the pouch.

The pouch can be fixed in position with the help of at least one chest strap and/or one shoulder strap or combined chest and shoulder straps. The pouch is preferably fixed in the area of the user's solar plexus.

In a particularly preferred embodiment of the invention, the pouch is fixed in the area of the user's manubrium. It is advantageous to record the position of the human body, in particular the degree of inclination of the human body, in this area of the body.

It is possible for the carrying device to be formed as an upper body garment. The carrying device may be in the form of a T-shirt or a long-sleeved shirt or undershirt. Preferably such a carrying device sits close to the body. The at least one position sensor, in particular the at least one body position sensor unit, and/or the at least one arithmetic unit and/or the at least one output unit for outputting an acoustic signal and/or the at least one output unit for outputting a vibration signal and/or the at least one display unit and/or the at least one control unit may be attached to the upper body garment, in particular sewn on and/or glued on and/or hook-and-loop fastened.

Furthermore, it is possible for the upper body garment to have at least one pocket and/or one slot in which the at least one position sensor, in particular the body position sensor unit, and/or the at least one arithmetic unit and/or the at least one output unit for outputting an acoustic signal and/or the at least one output unit for outputting a vibration signal and/or the at least one control unit and/or the at least one display unit are located.

The at least one position sensor, in particular the at least one body position sensor unit, is preferably arranged or fixed in the area of the user's solar plexus. In a particularly preferred embodiment of the invention, the at least one position sensor, in particular the at least one body position sensor unit, is arranged or fixed in the area of the manubrium.

The formation of the carrying device as an upper body garment is particularly suitable for forming multiple position sensors and arranging them at different positions and/or body parts of the user. Moreover, with the help of such a formed upper body garment, an output unit for outputting a vibration signal with multiple vibration generators can be formed. The vibration generators can be arranged at different positions and/or on different parts of the user's body.

A further formation of the carrying device can be formed stocking-like or band-like. Such a formation of the carrying device makes it possible to attach position sensors, in particular a body position sensor unit, to an extremity of the body. In another embodiment of the invention, it is possible to form the carrying device glove-like.

In another embodiment of the invention, it is possible to form the carrying device as part of a shoe or shoe-like.

The formation as an eyeglass adapter is also possible. Provided that position sensors are attached to eyeglasses, the user's head posture can be detected or monitored in particular. It is also possible to form an output unit for outputting an acoustic signal on eyeglasses. Such an embodiment of the carrying device allows a combination with already existing objects or devices of the user.

In a further embodiment of the invention, it is possible that individual elements of the inventive system, in particular position sensors, are attached or can be attached to the user's clothing as a kind of piece of jewelry, in particular in the form of chains or brooches. Such a formation of position sensors and/or vibration generators makes it possible to carry individual components of the system discreetly.

In yet a further embodiment of the invention, individual elements or components of the system can be attached or are attachable to a user's clothing by means of magnets. Such a magnetic attachment is preferably carried out by means of two magnets, with the user's clothing located between the two magnets. In this context, the user's existing clothing can serve as a kind of carrying device, whereby the clothing can be changed regularly. A magnetic attachment also serves for the individual positioning of individual elements or components of the system.

In yet a further embodiment of the invention, at least one sensor, in particular at least one position sensor, can be magnetically attached to a transdermal implant.

In a further embodiment of the invention, the inventive system may comprise an audio module. This audio module is preferably formed between the arithmetic unit and the output unit for outputting an acoustic signal.

In a particularly preferred embodiment of the invention, the audio module preferably comprises at least one tone generation unit and at least one audio mixer unit. In other words, the tone generation unit is the audio source. Using the tone generation unit, the fundamental tone of the at least one acoustic signal can be generated. This can be done in the form of a synthesizer or tone generator. The formation of an audio player is also possible. For example, audio files may be stored. In other words, it is possible to select from multiple stored tone sets of an audio player. However, it is also possible to generate an individual tone by means of a tone generator.

For example, it is possible for the tone to be generated on the Internet, in particular on a server, and streamed, in particular retrieved and received, by the arithmetic unit of the system and/or the audio module. This can be done, for example, via an Internet audio player, where the body position sensor unit and the audio mixer unit generate the acoustic signal, preferably in real time.

The audio mixer unit serves for forming sound effects and for converting sound. This can affect both the pitch and the tone phases. In particular, the stereo volume of the individual channels is controlled using the audio mixer unit.

For example, it is possible that the signal generated by the audio mixer unit is also generated on the Internet, especially on a server, and streamed by the arithmetic unit and/or the audio module. In terms of procedure, this can be done, for example, such that the arithmetic unit sends the body position data determined by the body position sensor unit to a server. Audio mixing and/or tone generation and/or conversion of body position data can be performed on a server.

The acoustic signal can be streamed, in particular retrieved and received, by the system's arithmetic unit and/or the audio module.

The system may also comprise a monitoring unit, in particular an external monitoring unit. This monitoring unit can be formed as a mobile communication device. The, preferably external, monitoring unit preferably comprises a control unit and a display unit. The display unit serves for visually displaying the data determined by the body position sensor unit. The control unit preferably serves for setting system parameters. The monitoring unit enables third parties, such as doctors or trainers, to monitor the application of the inventive system and intervene (in real time) with the application. Here it is possible that the system parameters are changed by external persons such as doctors or trainers.

With the help of the inventive system, it is possible, for example, to control the posture during sitting, in particular during longer periods of sitting. Thus, a correct sitting posture can be enabled. Furthermore, rehearsed or defined movement sequences, in particular in gait and posture, can be checked. The person can be given feedback so that the correct execution of the movement sequence and/or the movement sequence of individual limbs and/or an exercise is made possible even without the presence of a therapist and/or a doctor.

In yet a further embodiment of the invention, the system may comprise storage. The storage can be a local storage. This local storage is preferably integrated into the arithmetic unit of the system. Furthermore, it is possible for the storage to be an external database, in particular a cloud. The data collected by the body position sensor unit can be stored and/or transferred in the database. The external database can also be called a platform.

The system can also have a communication unit. With the help of the communication unit, collected data can be transferred to the database, in particular to a cloud or an online database or a web server. Furthermore, the communication unit is preferably configured such that data can be retrieved from a cloud, an online database or a web server and imported into the system, in particular into the arithmetic unit. This is data such as software updates, software upgrades, new tones and predefined presets and/or setting options.

The inventive method for posture and movement regulation for humans can also be described as a method for walking and movement regulation aid. Since the regulation of movement comprises a regulation of walking and gait and, furthermore, a regulation should also be enabled when the user is standing still, namely a regulation of posture, the method for walking or gait and movement regulation aid is referred to in the following as a method for posture and movement regulation for humans.

The inventive method is performed in particular by applying a system according to the invention. The inventive method for posture and movement regulation comprises the following steps:

a) determining the position, in particular of the body position data, of the human body, in particular determination of a degree of inclination of the human body, b) sending the position data, in particular the body position data, to an arithmetic unit, c) converting the position data, in particular the body position data, into at least one acoustic signal and/or at least one vibration signal, d) sending the acoustic signal to an output unit for outputting an acoustic signal and/or the vibration signal to an output unit for outputting a vibration signal.

Preferably, the inventive method is performed with the inventive system described above.

Steps a) to d) are preferably repeated infinitely while the inventive system is being carried. Step a) is preferably performed with the help of a/the body position sensor unit.

In step c), a comparison of the position data, in particular of the body position data, with target position data, in particular target body position data, may be performed. This step c) is preferably performed with the help of an arithmetic unit.

Prior to step a), a calibration step may be performed, in which the 0° position, in particular the 0° body position data, of the human body, in particular the 0° inclination of the human body, is determined.

Among other things, a calibration step is necessary to enable persons with a leaning basic body posture to use the inventive system as well. Moreover, the device is to be attached to the body quickly. However, since in most cases the device cannot or will not be mounted 100% vertically, it is necessary to determine the 0° position of the human body in the context of a calibration. In particular, the 0° position of the human body or the 0° inclination of the human body can be determined as a mean value. As an alternative, it is possible to set the absolute perpendicular as inclination grade 0.

In particular, the comparison of body position data with target body position data preferably performed in step c) can be performed on the basis of the 0° position of the human body determined in the calibration step. The target body position data can thus correspond to the 0° position of the human body, in particular the 0° inclination of the human body.

Prior to step a), in particular prior to the calibration step, a setting step (setting mode) can be performed. In the setting step, for example, presettings of the system can be made without prior positioning of a position sensor, in particular a body position sensor unit. Such settings are no longer possible or very difficult to make during the actual determination of the body position data and during movement.

In the course of the setting step, it can first be defined at which degree of inclination 1 (n1) an acoustic signal should be output. Furthermore, it is possible to define a degree of inclination 2 (n2) in the setting step, at which a maximum volume or an alarm tone in the form of an acoustic signal is output. Furthermore, it is possible to preset the system parameters such that a quickly responding and possibly loud or hard signal should be output or that a gently rising acoustic increase in one or both ear(s) should be generated. Furthermore, it is possible to set the overall volume separately, which is stored in a storage after setting the system parameters.

Preferably, at least two presettings are made in order to convert only the individual and relevant range of motion or inclination of the human body into signals, in particular into acoustic signals.

This is a first sensor value, which for example corresponds to a first inclination value. The first sensor value (n1) defines the smallest sensor value that must at least be exceeded in order to start an acoustic signal and/or an acoustic increase.

A/the second sensor value (n2) can correspond to the second inclination value. The second sensor value defines the maximum sensor value at which an acoustic increase is to be reached maximally. An acoustic increase is to be understood, for example, as the pitch or volume of the acoustic signal. In this context, sensor values thus are values to be detected by means of a sensor.

The two sensor values (n1, n2) can each be determined or defined for a movement to the left and to the right. The two sensor values (n1, n2) can each be determined or defined for a movement forward and backward.

This allows the sensor values (n1, n2) to be determined or defined from two sides, i.e. for left and right or for front and rear symmetrically to a mean body reference axis. This means that the two sensor values (n1, n2) are only determined for one side (e.g. left) and then the two sensor values (n1, n2) for the second side (e.g. right) are defined symmetrically to these.

In yet a further embodiment of the invention, it is possible to first determine the sensor values (n1, n2) for a first side and then for the second side. Thus, the sensor values (n1, n2) can be determined independently of each other with regard to the respective sides.

In a first embodiment of the inventive method, the presettings can be made in the setting step by means of a control unit. It is possible for the user to orient himself on possible settings or on a selection of predefined system parameters and thus to define the first sensor value (n1) and the second sensor value (n2).

In a further embodiment of the inventive method, it is possible that the setting step is not performed in the sense of a presetting to be typed in or a presetting to be selected from a multitude of presettings. The setting step is possible in this embodiment of the inventive method without sight of or without viewing a control unit. In this embodiment, the presetting or setting step can be performed by tapping on a control unit. In this process, the user orients himself on a real-time body inclination. While this real-time body inclination is performed actively by the user, a first sensor value and a second sensor value can be set each by confirmation on the control unit, i.e. by blind tapping. In this case, the control unit serves as a kind of response button, i.e. as a feedback button.

In step a), the body position data can be determined in the sagittal plane and in the frontal plane of the body. In this context, the sagittal plane refers to a plane extending from the head to the pelvis and from the back to the abdomen. The frontal plane is the plane of movement visible in a frontal view of the human being. In connection with the sagittal plane, the body position data thus is recorded in the sense of an extension from front to back or vice versa. In connection with the frontal plane, the body position data is recorded in an extension from left to right or vice versa.

In step c) a first acoustic signal can be generated for the body position data in the frontal plane and a second acoustic signal for the body position data in the sagittal plane. In other words, when the body is inclined to the left or right, a first acoustic signal, in particular a first tone, in particular a first stereo sound, can be generated. When the body is inclined forwards or backwards, a second acoustic signal, in particular a second tone, particularly preferred a second stereo sound, can be generated.

In other words, a tone in the respective ear, i.e. in the left or right ear, that increases with the degree of inclination within a defined range, and an additionally changing stereo sound character (front, back) can be used to intuitively inform the user acoustically in real time in which direction and to what extent the body's inclination is currently formed. Depending on the presettings, the tone may increase slowly or quickly.

It is possible to create a so-called base tone. Such a base tone is output via the output unit for outputting an acoustic signal even if there is no deviation from the 0° position of the human body, in particular no deviation from the 0° inclination of the human body. The volume of the base tone can be extremely low. A base tone is used to perceive the generated tone differences more sensitively. Moreover, the base tone serves to achieve permanent system control. If no basic tone is output, the user can conclude that the system is not functioning or that there is a fault.

Preferably, the position data, preferably the body position data, is stored. Moreover, it is possible to send the position data, in particular the body position data, to a database.

The position data, in particular the body position data, can be stored in the inventive arithmetic unit. Moreover, it is possible for a mobile communication device to have a storage for storing the position data, in particular the body position data. The formation of an external storage is also possible.

If the position data, in particular the body position data, is sent to a database, it is preferably an external database. The database can be a cloud.

Furthermore, it is possible to save automatically captured data or to send it to a database. Automatically captured data may be, for example, the time and/or the date and/or the weather conditions and/or the temperature and/or a GPS signal and/or motion and vibration values and/or the distance traveled and/or the system usage time and/or the speed of movement and/or information on soil conditions and/or the system settings used, in particular the defined sensor thresholds. This makes it possible to correlate the stored body position data with external conditions.

Moreover, it is preferably possible to save manually created notes of the user or to send them to a database. Manually created notes may be, for example, the user's clinical picture and/or the user's current medication and/or the user's general health status. This allows an analysis mode to be performed. Therapy progressions can be recorded and optimized.

By means of a tone, which is associated with the degree of inclination of the body, in the respective ear of a user, the user, in particular of the inventive system, is informed acoustically in which direction the body is inclined and/or to which extent the body is inclined.

In other words, an acoustic signal, which is associated with the deviation of the body from the 0° position of the human body, in the respective ear of a user can inform the user in which direction the body deviates from the 0° position of the human body and/or how much the body position deviates from the 0° position of the human body.

The acoustic signal can also be a mute signal. If no tone, in particular no stereo acoustic signal, is output, the position/inclination of the body does not have to be corrected. The same applies to the output of a vibration signal. If the position/inclination of the body does not have to be corrected, it is possible not to output a vibration signal.

A first method for converting the body position data into an acoustic signal provides for a mono rise. If a changed acoustic signal is sent to an ear, in particular an acoustic signal which changes with regard to volume or modulation or with regard to effects, the position of the body must be corrected. If no acoustic signal is output by the output unit or only the base tone is output by the output unit for outputting an acoustic signal, the body position or the inclination of the body does not have to be corrected.

A further embodiment of step c), i.e. the conversion of the body position data into at least one acoustic signal, provides for a stereo change to be performed. Accordingly, when a 0° position of the human body is adopted, in particular a 0° inclination of the human body, a central, equivalent stereo signal is output to both ears of the user. In other words, a stereo signal is output in equal proportions to the left and to the right ear of the user. When the body position has to be corrected, in particular in case of an inclination of the human body to be corrected, the acoustic signal is increased in one ear and reduced equivalently in the other ear.

The inventive method provides in particular for an acoustic signal, in particular a second acoustic signal, to be output by the output unit also if the body position deviates forwards or backwards. The second acoustic signal can increasingly replace the first acoustic signal depending on predefined settings and/or depending on the actual degree of inclination.

Depending on the personal sensation of the user and the therapy goal, the acoustic signal can generate a kind of pressure resistance or a kind of suction effect on the user.

In a pressure resistance type method, the volume of the tone increases in that ear of the user to which side the user's body is inclined.

In other words, when the body is inclined to a first side, the volume of the tone in the ear of that first side increases. The tone thus signals the actual situation of the body position or the inclination status of the user's body.

After a familiarization period, the user perceives the acoustic signal output as an increasing resistance and an increasing warning.

In a suction type method, the acoustic signal is generated on the ear opposite the direction of inclination. After a familiarization period, the user perceives such an acoustic signal output as a soft, pleasant correction and less as a warning.

The pressure resistance type method or the suction type method can be performed alternatively or additionally with vibration signals.

In a further embodiment of the invention it is possible that in step a) the average direction of movement of the body and a deviation from the average direction of movement are determined. It is possible for a user to have a crooked gait pattern without the body position deviating from the 0° body position or the body being inclined in a certain direction. It is therefore possible for a user to deviate from the average direction of movement despite a straight upper body, in other words despite a straight posture, for example as a result of swaying steps. Therefore, it is possible that users can be informed of deviations from the average direction of movement by means of an acoustic signal and/or a vibration signal. This requires the average direction of movement of the user to be identified or detected first.

Even when deviations from the average direction of movement are included in the conversion (step c)) of the body position data into at least one acoustic signal and/or one vibration signal, a setting step (setting mode) preceding step c) can be performed.

Therefore, a setting step (setting mode) can be performed prior to the calibration step.

In the course of the setting step, it can first be defined at which degree of deviation (a1) from the average direction of movement an acoustic signal should be output. Furthermore, it is possible to define a degree of deviation 2 (a2) in the setting step, at which a maximum volume or an alarm tone in the form of an acoustic signal is output. Furthermore, it is possible to preset the system parameters such that a quickly responding and possibly loud or hard signal should be output or that a gently rising acoustic increase in one or both ears should be generated.

Also, performing the setting step, i.e. either selecting presets from a variety of available presets or making adjustments on the basis of real-time movement, can be done in the context of the degree of deviation as described above in the context of the degree of inclination.

As an alternative and/or in addition to an inclination value, the deviation from the average direction of movement can be played back acoustically. The option regarding the inclusion of the deviation from the average direction of movement can be formed to be switchable on and off.

In a further embodiment of the invention, it is possible, when determining the body position data in step a), to collect data regarding the step force, which can also be referred to as step strength or tread force. Step force or step strength or tread force is to be understood as the force with which the foot hits the surface when walking. The step force is detected by the inventive system as body tremor, for example. Preferably, the body position sensor unit for detecting this body tremor comprises at least one tremor sensor.

The data regarding the step force can be considered in step c), i.e. when converting the body position data into at least one acoustic signal and/or one vibration signal. In other words, the data regarding the step force can be included in the calculation of the acoustic signal and/or the vibration signal.

It is possible to output this step force data during the generation of the acoustic signal in amplified form as compared to the acoustic signals associated with body inclination data. This serves in particular to amplify acoustic signals with regard to the gait pattern. The user can thus obtain information about his/her gait pattern.

Furthermore, it is possible not to include or actively filter out the step force data when generating the acoustic signal. For users who only want to receive information about body sway, the additional outputting of an acoustic signal in connection with the step force can be disturbing. The user can better concentrate on body sway and compensation of body sway when the step force signal is filtered out.

In a further embodiment of the invention, in step a) data regarding the step length and/or the time duration of the ground contact of the two feet and/or the push-off height of the feet can be recorded. This data can be considered in step c), i.e. when converting the body position data into at least one acoustic signal and/or one vibration signal. In other words, the data mentioned can be included in the calculation of the acoustic signal and/or the vibration signal.

Furthermore, it is possible that the body position data determined in step a), in particular the determined inclination degree data, is converted into a visual image and sent to a display unit and/or stored in a database.

The task is further accomplished by a computer readable storage medium containing instructions that cause at least one processor to implement an inventive method according to one of the preceding embodiments when the instructions are executed by the processor.

This results in similar or identical advantages to those already described for the method described above.

In addition or as an alternative, reference is made to the schematic diagrams which describe (in more detail) the inventive system for walking and movement regulation aid, in particular the inventive system for posture and movement regulation, and/or the inventive method for walking and movement regulation aid, in particular the inventive method for posture and movement regulation for humans.

These are as follows:

BRIEF DESCRIPTION OF THE SEVERAL VIEWS OF THE DRAWINGS(S)

Figure 1B:
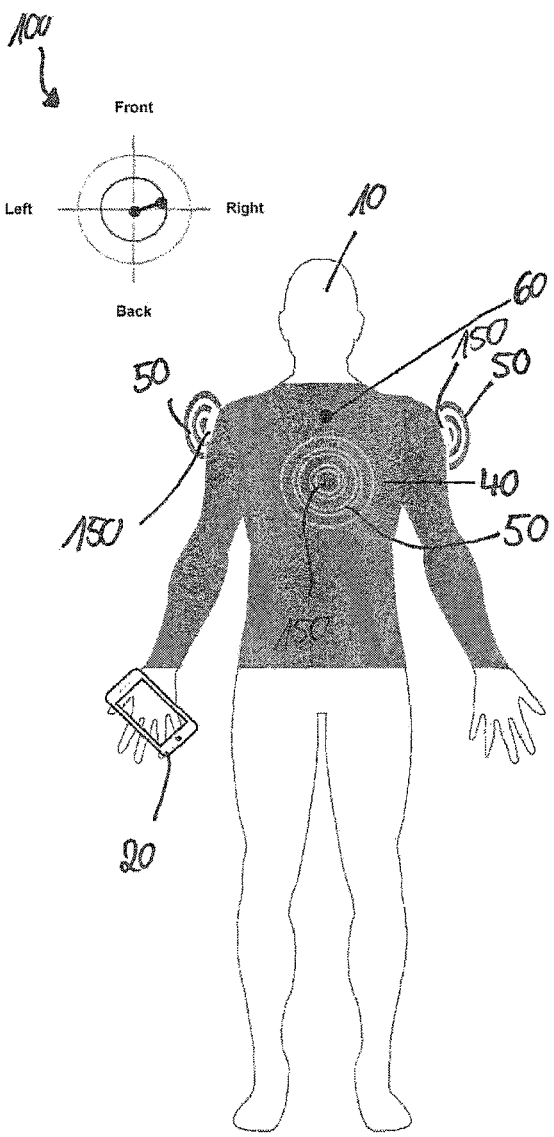
Figure 2A:
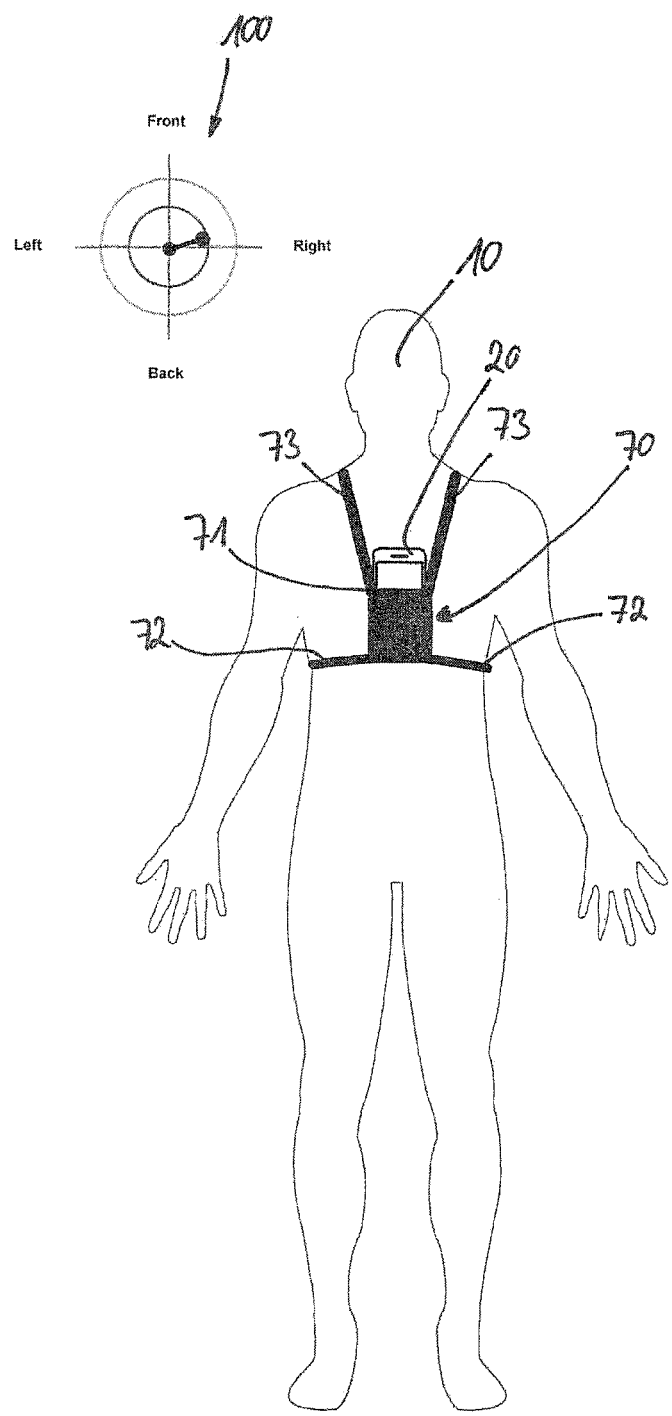
Figure 2B:
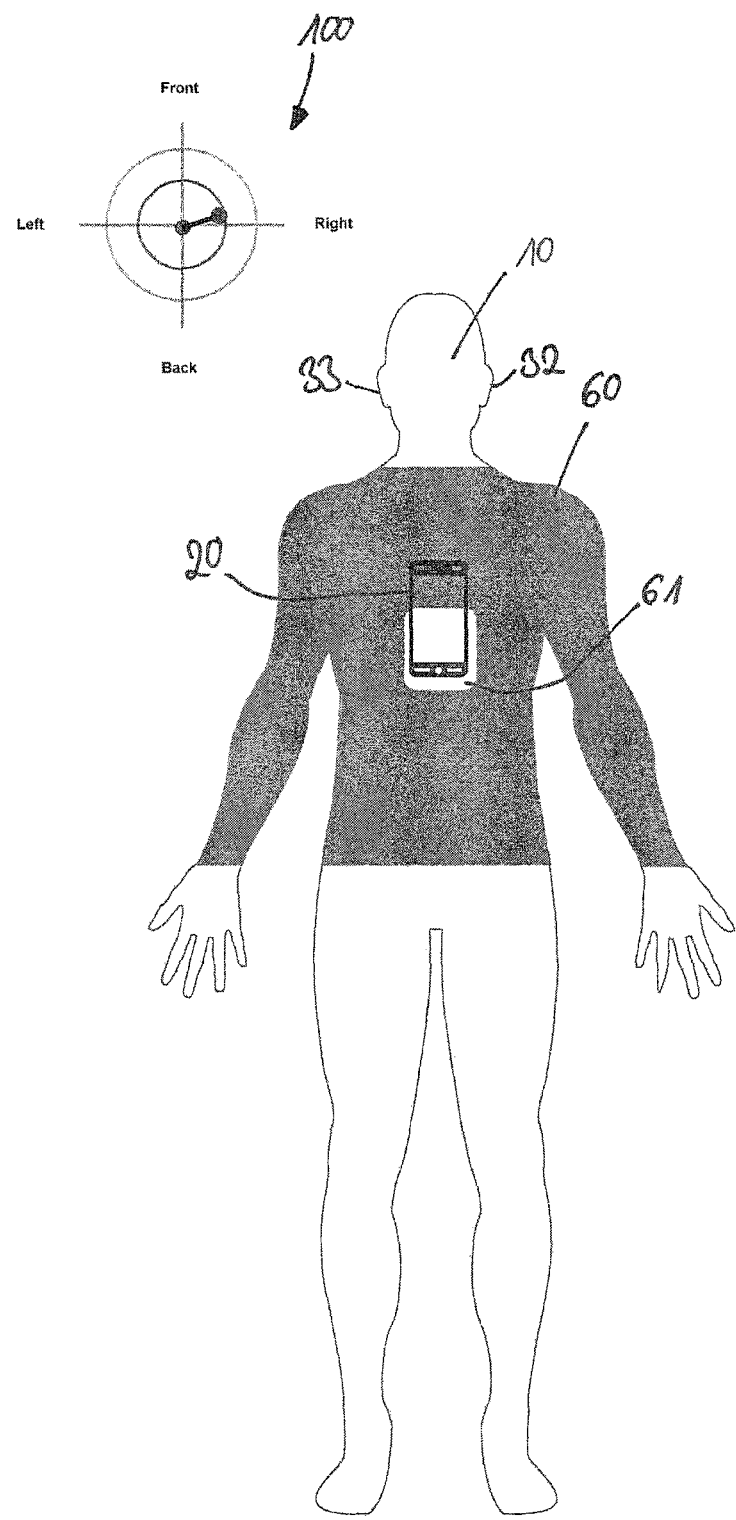
Figure 2C:
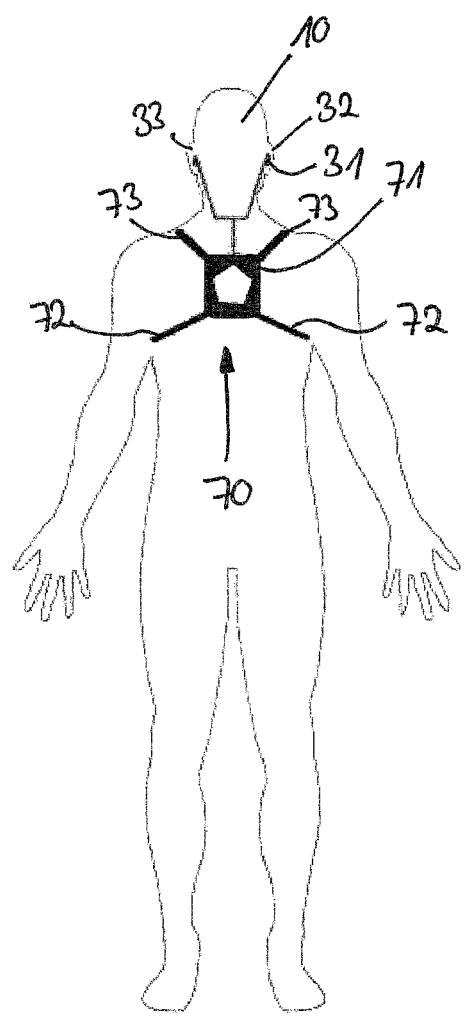
Figure 6:
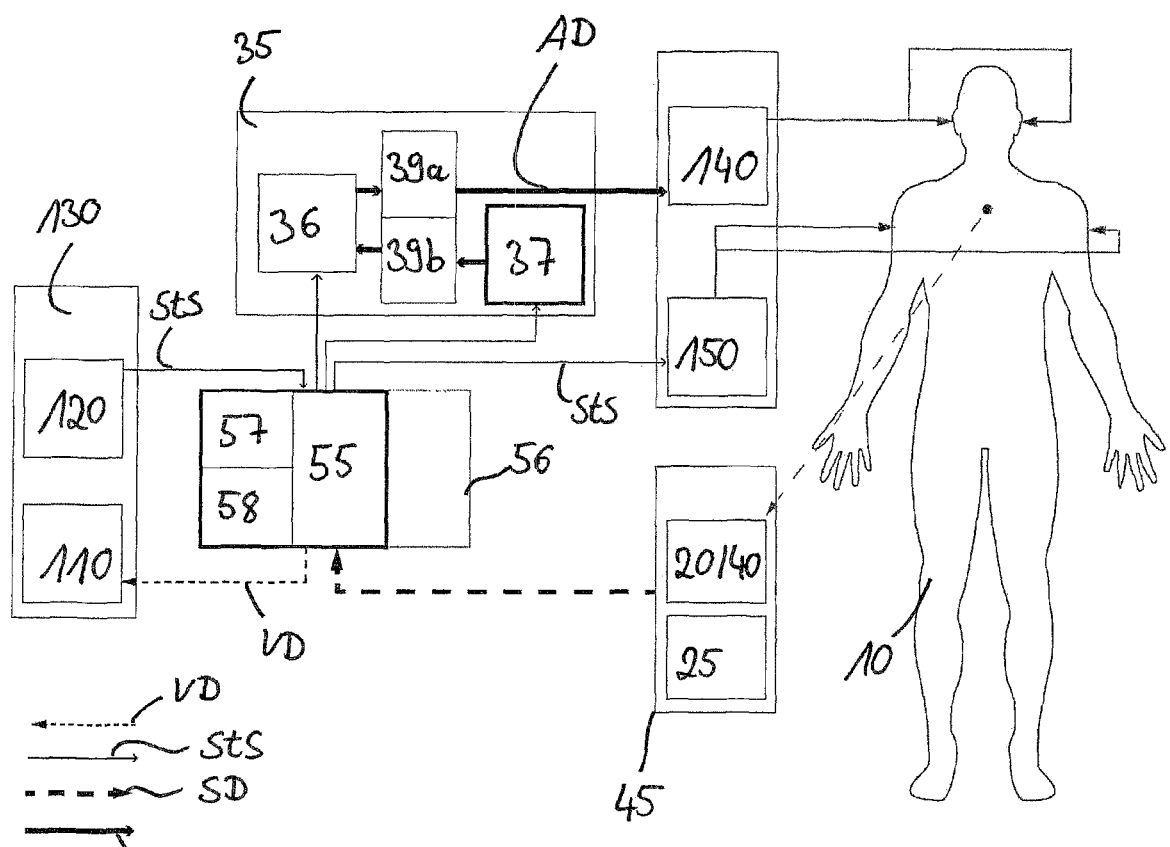
Figure 7A:
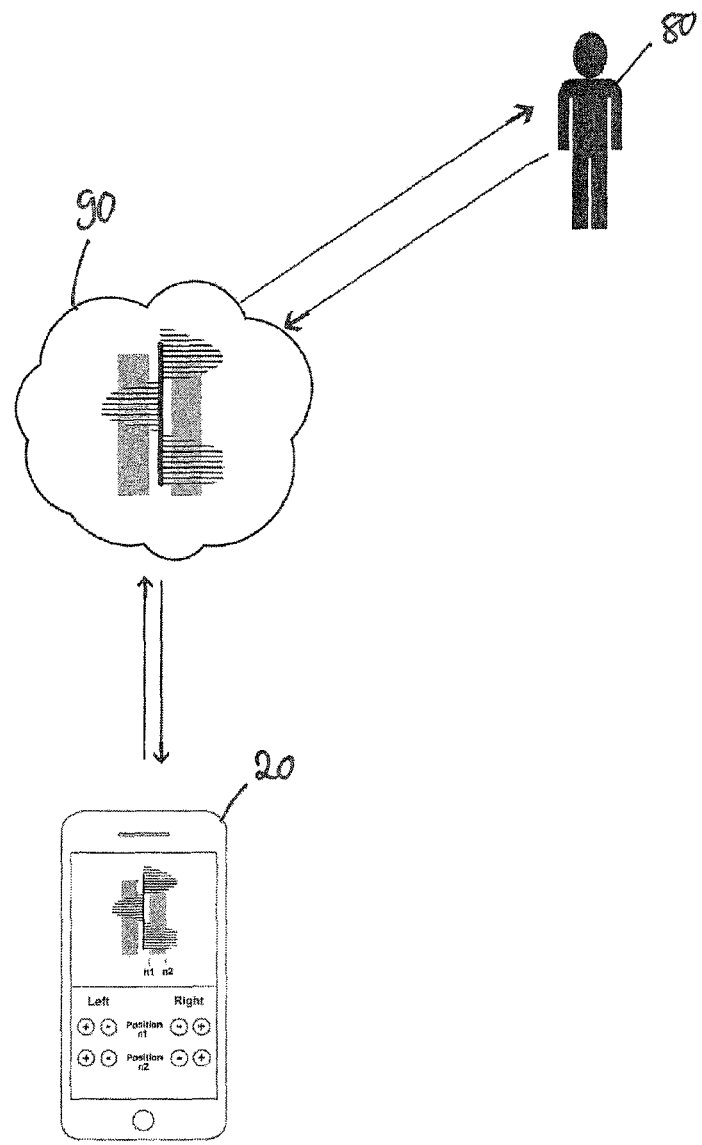
Figure 7B:
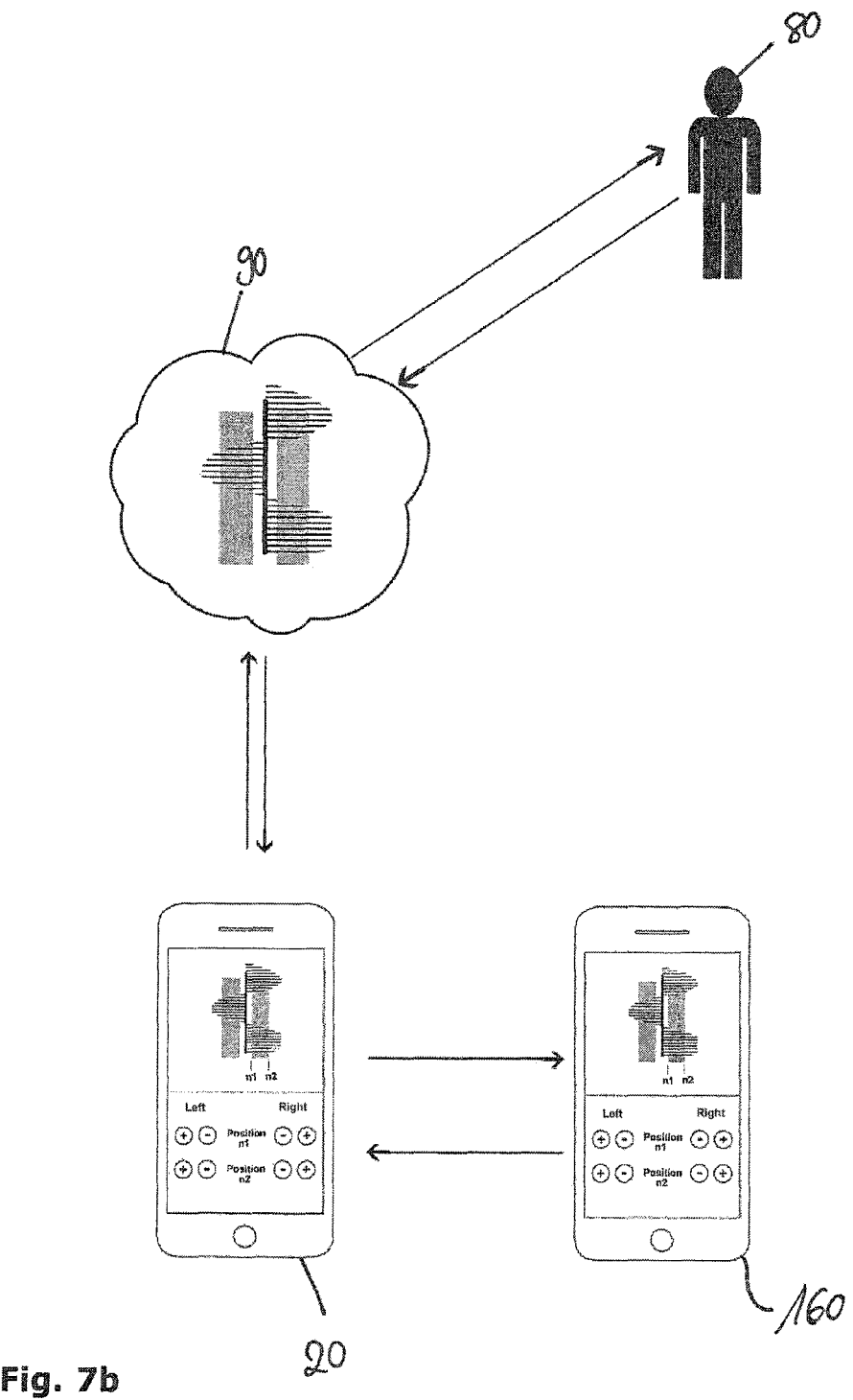

FIGS. 1a and 1b a schematic diagram of the inventive system for posture and movement regulation;

FIGS. 2a to 2c various illustrations of carrying devices of the inventive system;

FIGS. 3a to 3d exemplary representations on the display unit;

FIGS. 4a to 4e various representations on a control unit depending on the respective process step carried out;

FIGS. 5a to 5e schematic diagrams regarding the conversion of the body position data into at least one acoustic signal and/or one vibration signal;

FIG. 6 an overview of potential elements or components of the inventive system; and FIGS. 7a and 7b an illustration of further connection possibilities to an inventive system for posture and movement regulation.

DETAILED DESCRIPTION OF THE INVENTION

In the following, the same reference numerals are used for identical or equivalent parts.

As shown in FIG. 1a, inclination data from position sensors of a mobile communication device attached to the body 10, in particular of a smartphone 20, is converted into acoustic, in particular stereo acoustic signals 30. In the smartphone 20 all necessary elements of the inventive system are formed. The necessary elements are at least one position sensor, in particular a body position sensor unit. An arithmetic unit is also integrated in the smartphone 20. Furthermore, an output unit for outputting an acoustic signal, in this case a stereo acoustic signal 30, is formed.

In this case, the output unit is a headphone 31. Position sensors directly or indirectly attached to the body 10 or a body position sensor unit can send data regarding the position and/or inclination and/or rotation and/or posture as well as changes in position and/or inclination and/or rotation and/or posture to the arithmetic unit of the smartphone 20. This data is converted in real time into at least one acoustic signal and/or one vibration signal. In the present case, the data is converted into stereo acoustic signals. The stereo acoustic signals 30 are output or perceived in the left ear 32 and/or in the right ear 33. The user can react to the stereo acoustic signal and change the body position. In the present case, the position sensors are integrated into the smartphone 20. Moreover, smartphone 20 may comprise an output unit 150 for vibration signals. This is indicated schematically by the emitted vibration signals 50.

As shown in FIG. 1b, a position sensor 40 can be connected to a mobile communication device, in particular a terminal device 20 with Internet access, for example using a radio connection. The position data/inclination data, in particular the body position data, is converted into vibration signals 50 in the example shown. On the screen of the mobile communication device, in particular of the smartphone 20, a visual representation 100 can show the position of the user's body 10 or the extent to which the user's body 10 is inclined.

Since multiple vibration generators are attached to the carrying device 60, vibration signals can be emitted at different points of the body.

In FIG. 1a, the stereo acoustic signals are perceived via a headphone 31, in-ears or bone conduction headphones, via cable or BLUETOOTH short-range wireless communication technology standard directly at the ear, especially at the two ears 32 and 33. Vibration signals can be triggered in FIG. 1 directly via the smartphone 20 and transmitted to the body 10. In FIG. 1b, on the other hand, alternative external BLUETOOTH short-range wireless communication technology standard vibration generators 150 are arranged in close proximity to the body 10.

The goal of this inventive system/method is to give patients with balance disorders, during rehabilitation phases after accidents/operations or in the case of incorrect postures to be corrected additional, easily understandable feedback on their own posture or inclined position or body inclination and, in addition, to bring about a safe feeling and sense of stability in the user through the learning effect of the "new sense". Moreover, the movement data can be made available to the user or doctors or researchers or trainers or physiotherapists.

In FIG. 1*b*, a carrying device 60 is formed in the form of a long-sleeved shirt. Position sensors 40 and BLUETOOTH short-range wireless communication technology standard vibration generators 150 are integrated into the carrying device 60, e.g. by gluing, sewing or hook-and-loop fastening.

As regards position and use on the body, it should be noted that a smartphone 20 optionally may also be attached either to the front of the body or to the back using a carrying device 70, as shown in FIG. 2*a*. This carrying device 70 optionally contains a battery extension/additional battery for smartphones. The carrying device 70 is formed as a pouch 71 with a waist strap 72 and shoulder straps 73.

In connection with the sensors, in particular the position sensors, in particular the body position sensor unit, it should be noted that the inclination sensor data "front", "back", "left" and "right", which are picked up by the smartphone 20, are picked up in degrees in real time via an application (app) and displayed visually. Illustration 100 shows that the body is slightly tilted forwards to the right. The application is preferably associated with a computing program stored in the arithmetic unit of the inventive system.

FIG. 2*b* again shows a carrying device 60 in the form of a long-sleeved shirt. This carrying device 60 has a pocket 61. This pocket 61 can hold a smartphone 20. The Smartphone 20, in turn, integrates all the necessary components or elements of the inventive system. These are the body position sensor unit, the arithmetic unit as well as the output unit for outputting an acoustic signal. In the example shown, headphones are not connected to the smartphone 20 by cable, but by radio.

FIG. 2*c* shows another carrying device 70. This, in turn, comprises a pouch 71. A mobile communication device can be located in this pouch 71. As shown in FIG. 2*c*, pouch 71 is arranged on body 10 such that it is located in the region of the manubrium. Thus, the body position data of body 10 can be detected in the area of the manubrium. Detection is performed by a communication device located in pouch 71, which comprises a body position sensor unit.

Figure 3A:
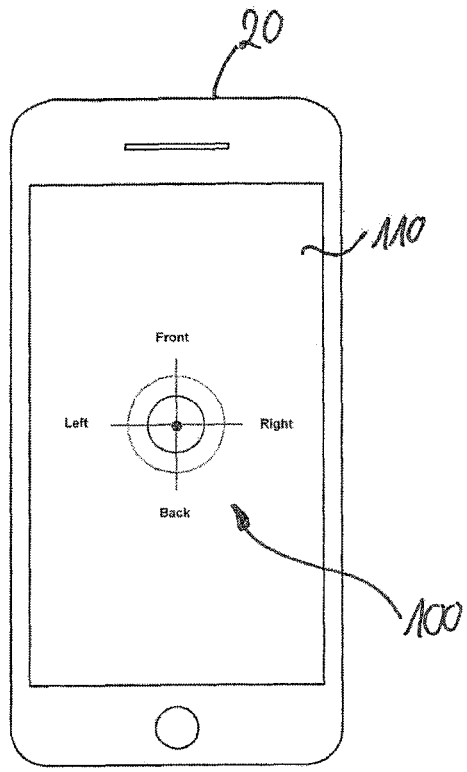
Figure 3B:
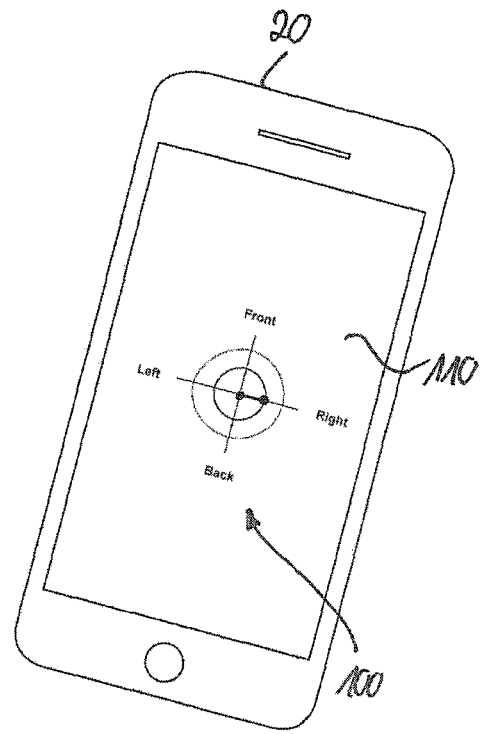

FIGS. 3*a* to 3*d* show exemplary representations 100 on the mobile communication device 20. The 2-axis representations shown in FIGS. 3*a* and 3*b* are similar to a spirit level view from above (circular level). In these representations 100, when walking, the movements on both axes, i.e. the movements in the sagittal plane and in the frontal plane, are represented in a view 100. This enables a better assessment of a course of movement. In FIG. 3*a* the body is in a 0° position. It is thus not necessary to adjust the body position 10.

FIG. 3*b*, on the other hand, indicates an inclination of the smartphone 20. The position sensors integrated into the smartphone 20 thus detect a deviation from the 0° body position. The representation 100 therefore shows that there is an inclination to the right. In FIGS. 3*a* and 3*b* the screen of the smartphone is used as display unit 110 of the inventive system. The display unit 110 serves for the visual display of the data determined by the body position sensor unit.

Figure 3C:
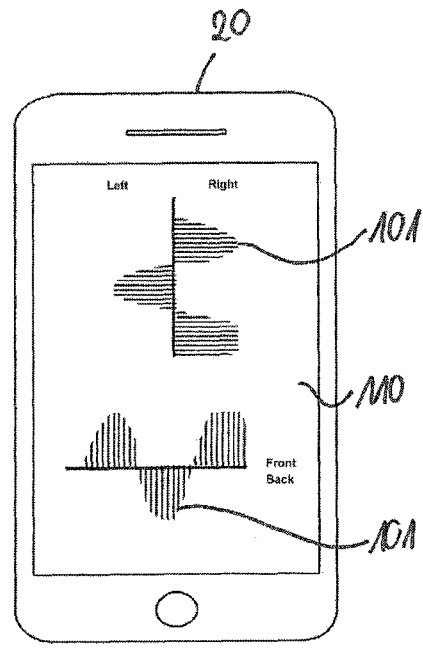

In FIG. 3*c* the screen of the smartphone 20 is also used as display unit 110. In this case, movements are represented by a motion scale or graphs 101. With the help of such a motion scale or such graphs, older stored motion scales can be compared with the current motion scale. Moreover, the motion scale or graphs 101 can be compared with previously set ranges of motion.

Figure 3D:
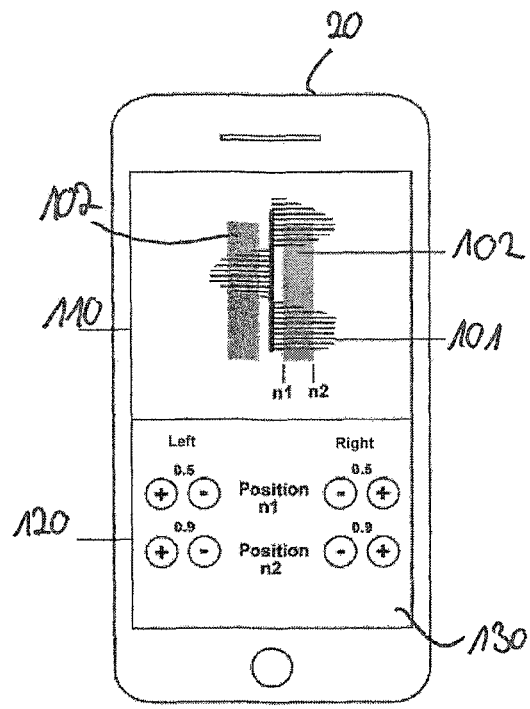

FIG. 3*d* again shows the screen of a smartphone 20. The screen serves both as a display unit 110 and as a control unit 120. A graph 101 as shown in FIG. 3*c* is represented on the display unit 110. Furthermore, active ranges 102 are represented on the display unit 110. The active ranges 102 are defined as the inclination ranges or deviation ranges from the 0° body position, in which acoustic signals are preferably output. The active ranges 102 are preferably defined in a setting step.

The setting step (setting mode) can be performed without attaching position sensors or without attaching a body position sensor unit. A first possibility for defining the active ranges is with the help of the control unit 120. In this process, first sensor values or first inclination values (n1) are defined. These are the smallest detected deviations from the 0° body position which must be at least exceeded in order to trigger the output of an acoustic signal.

Furthermore, second sensor values, in particular second inclination values (n2), must be specified. These inclination values n2 define the maximum degree of deviation from the 0° body position at which the maximum acoustic signal is output. This can be described as maximum in terms of pitch or duration.

The setting step in connection with the control unit 120 can be performed such that the user orients himself on the possible setting values and their visualized ranges in the control unit 120 and defines the threshold sensor values n1 and n2 by changing the values, namely by pressing the plus or minus keys. The additionally shown graph 101 visualizes the occurred movement data and serves to compare the fine adjustments.

A further embodiment of a setting step provides for the minimum and maximum values to be defined or for the first and second sensor values (n1, n2) to be defined by simply tapping on the control unit 120. To perform the setting step according to the second embodiment, it is first necessary to start the setting step or setting mode in the control unit 120. Subsequently, the user performs a real-time body inclination and defines the minimum and maximum values, i.e. the first and second sensor values, based on this. This may be performed as follows, for example:

First, a slight inclination to the first side (left or right) takes place. The first sensor value ($\triangleq$ inclination value 1=n1) can be set by confirming the slight body inclination. In this context, the user does not have to hit a special key or field on the control unit 120, but can simply confirm this inclination value by tapping on the control panel 120. In this connection, the control unit 120 serves as a kind of feedback button.

Subsequently, a stronger body inclination is performed in the selected direction (left or right). By tapping on the control panel 120, the second sensor value ($\triangleq$ inclination value 2=n2) is confirmed in turn.

In the presetting, the defined sensor values 1 and 2 for the other side of the body (left or right) can then be mirrored. On the remaining side, the same values n1 and n2 are set accordingly as for the previously defined values n1 and n2.

It is also possible to set the sensor values 1 and 2 for the other body side separately from the first body side.

In one embodiment of the invention, it is possible for the setting step (setting mode) to be explained by a voice message, so that the individual steps, such as the initial slight inclination and the subsequent stronger inclination, can be carried out step by step on the basis of the voice message. The setting step according to the second embodiment may also be referred to as quick tap configuration. A therapist and/or a physician and/or a researcher can also use this second embodiment of the setting step. This can be done, for example, by a/the monitoring unit.

As shown in FIG. 3d, the display unit 110 and the control unit 120 can be present in a combined fashion within one input and output module 130.

FIGS. 4a to 4e show the various control units and/or display units of the system as they are present in connection with different process steps.

As regards the sound or the acoustic signal as well as the inclination, the following should be explained: Depending on the therapy recommendation or one's own feeling, the beginning of the rising tone can be set at inclination level 1 and the maximum volume at inclination level 2 in each direction (see FIG. 4a). In this way, either a quickly reacting signal or a softly starting acoustic increase can be generated for each ear. The overall volume preferably can be set separately.

Figure 4A:
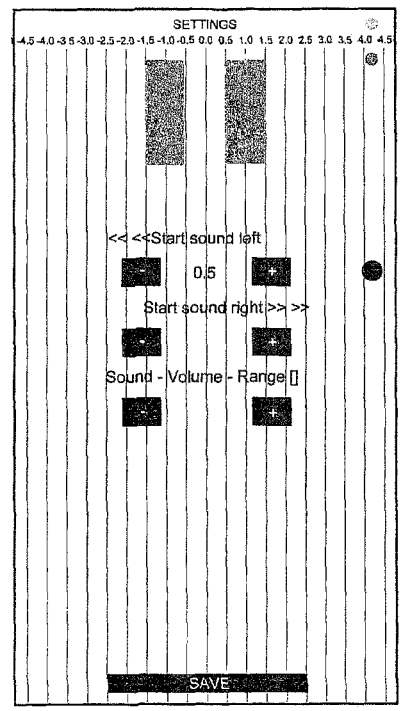
Figure 4B:
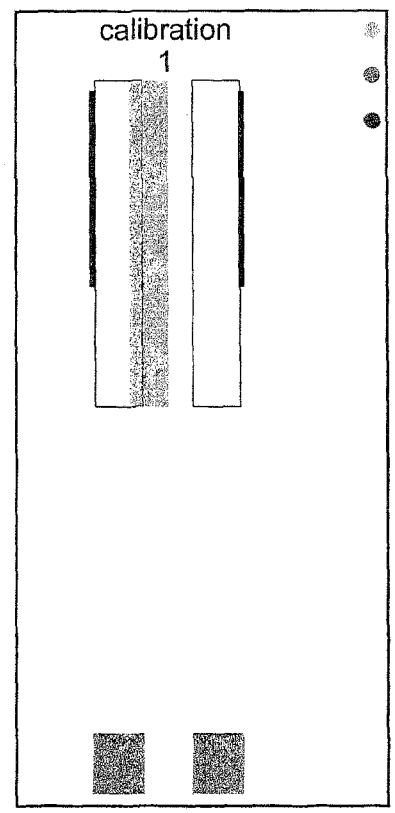

FIG. 4b shows the calibration step and the start of the inventive method. As regards the calibration and start, the following should be explained: A calibration process may be performed prior to the start of any use, whereby this concerns both use with recording and use without recording. The calibration process or calibration step may take five seconds, for example.

This makes it possible for persons with a leaning basic posture to use the system/method/app. The at least one position sensor 20/40 can be attached quickly to the body 10, whereby it will probably never be installed 100% vertically by the user and in the present case does not have to be installed 100% vertically.

During the calibration process, the user can position himself as upright as he feels most comfortable. A mean value is determined, which is then defined as inclination grade 0.

Figure 4C:
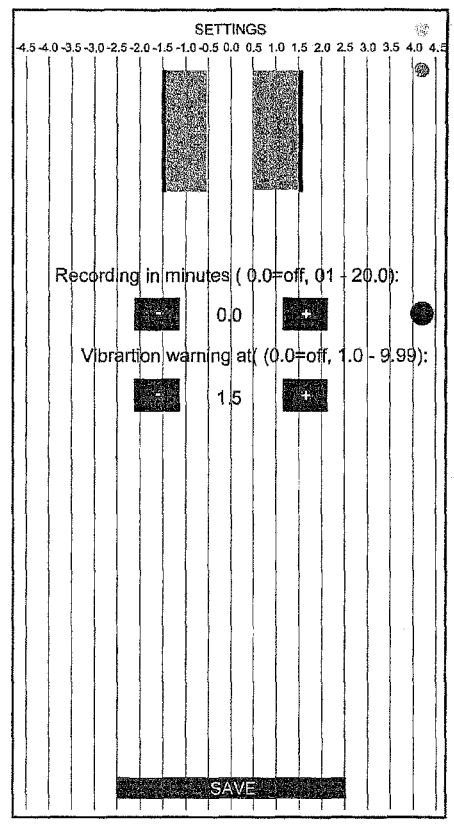

The possibility of outputting a vibration signal is also shown. As regards the vibration as a warning signal in addition to acoustic signals in the application, the following should be explained: A maximum inclination value per inclination direction can be defined in the application as a warning indication or for therapeutic measures. If this is exceeded, a vibration signal is preferably output at the center of the body (FIG. 4c).

As regards the vibration and inclination with alternative or external sensors/devices, the following is explained: When using external BLUETOOTH short-range wireless communication technology standard vibration sensors, these are preferably arranged on the shoulders or assigned to the shoulders (see FIG. 1b). These vibration signals can replace the function of increasing acoustic signals if the patient's ears are unsuitable as feedback receivers.

As an alternative or in addition, it is possible to attach a vibration generator to a person's temple or to a spectacle frame.

As regards an analysis recording mode and storage in a database, the following is explained: If the analysis mode is selected (see FIG. 4d), the user's movement data is recorded and visualized in a local database. Furthermore, it is possible for the recording to take place in an external database, for example cloud based. This can be done on the basis of a spirit level view from above (circular level) (see FIG. 3a). It is also possible to store and/or send to a database notes manually created by the user, such as medication, and/or automatically collectable data, such as GPS signals, weather data, etc.

Figure 4D:
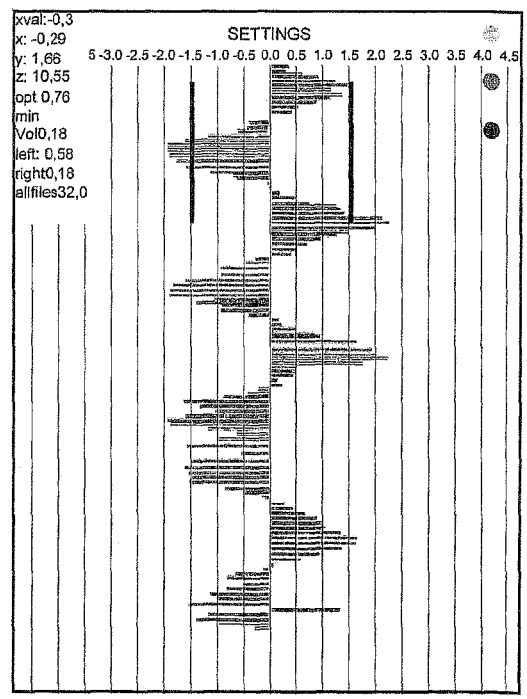
Figure 4E:
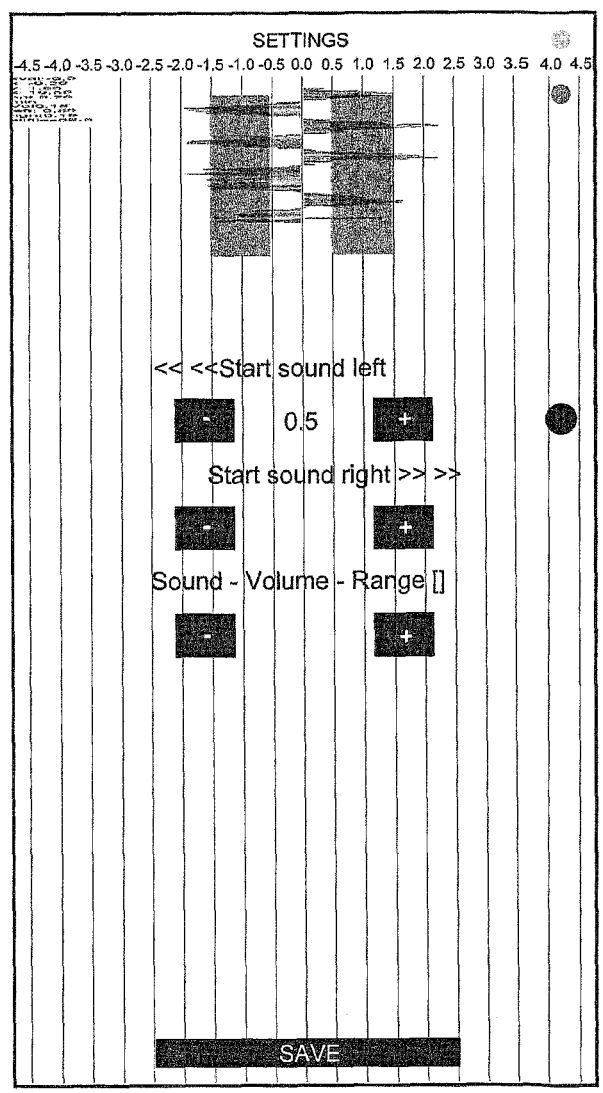

Optionally, the data can be made available to doctors or researchers or therapists or trainers via an online database (see FIG. 4d). Preferably, an analysis diagram is created and used as a background in the setting window (see FIG. 4a), which should serve the user as a visual aid for further optimizations (see FIG. 4e).

In principle, acoustic signals are played back 20 via headphones, which are connected to the smartphone via cable or BLUETOOTH short-range wireless communication technology standard, for example.

As regards the acoustic feedback obtained in this way, the following should be explained: Through a tone in the respective ear that increases with the degree of inclination, the user is informed acoustically in real time in which direction and to what extent he is currently inclined, by means of changing volume (left, right) and stereo sound character (front, back).

Depending on the personal sensation or therapy goal, the signal can generate a pressure resistance or a suction effect on the user.

As regards pressure resistance, the following should be explained: A low tone increases above the volume in the ear to which side the body is inclined. This means: inclination of the body to the right; the tone in the right ear becomes louder. The user often perceives this as increasing resistance (safety, stability) and increasing warning after a familiarization period.

As regards the suction effect, the following must be explained: A tone is played on the ear exactly opposite to the direction of inclination. The user may perceive this as a soft, pleasant correction after a period of familiarization, rather than a warning.

Optionally, the pressure and suction effect(s) can also be used for (external) vibration generators, as shown in FIG. 1b, for example.

In connection with the pressure or suction effect, the following should be explained additionally: Depending on the sensation of the user or the therapy recommendation, the direction of inclination and the acoustic side of the tone (left ear, right ear) can also be reversed.

The inventive process steps a) to d) are shown schematically in FIGS. 5a to 5e. In particular, step c), namely the conversion of the body position data into at least one acoustic signal, is illustrated here.

Figure 5A:
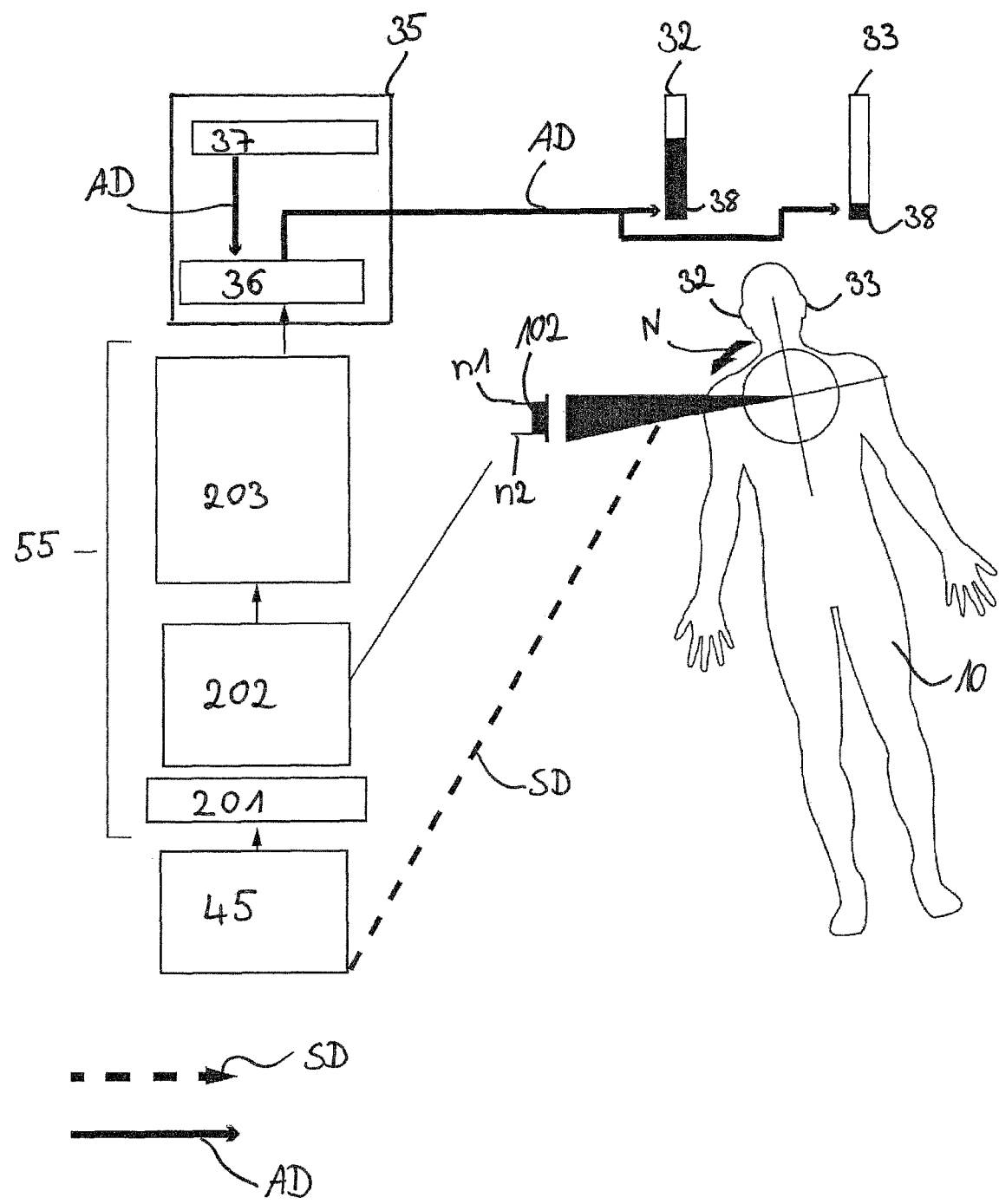

Body 10 has an inclined posture. The inclination or movement is represented by arrow N. The inclination values n1 and n2 can also be seen. These define the active range 102, as already explained in connection with FIG. 3d. The body position data is determined with the help of a body position sensor unit. In FIG. 5a, body 10 is shown in a posterior view.

The body position data is sent as sensor data SD from the body position sensor unit 45 to the arithmetic unit 55. This can be done either via a radio link or via a cable. The sensor data is accepted in step 201. Subsequently, in step 202, the received sensor data or sensor values are compared with the previously defined sensor thresholds n1 and n2. In step 203, the sensor data SD, i.e. the body position data, is converted into control signals for generating an acoustic signal.

This signal is then sent to an audio module 35. This may comprise both an audio mixer unit 36 and a sound generation unit 37. Furthermore, it is possible that the sound generation unit 37 forms a separate unit from the audio mixer unit 36. The sensor data converted into control signals in step 203 is sent to the audio mixer unit. At the same time, a stereo audio signal can be generated in the sound generation unit 37. This is, for example, a continuous tone. Alternatively, the generation of tone sequences or a piece of music is possible. This stereo audio signal, in particular the audio data AD, can influence a left or right channel simultaneously using the audio mixer unit 36. The modified stereo signal can be transmitted to the left ear 32 and to the right ear 33, for example through headphones, or can be output there.

Figure 5B:
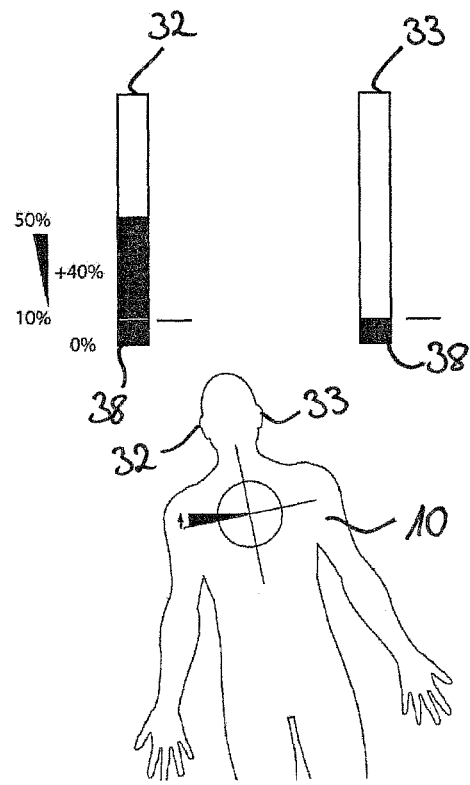
Figure 5C:
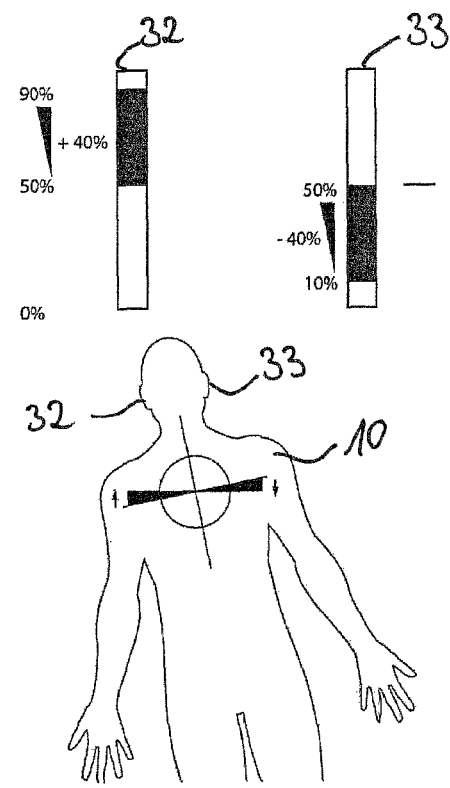

As shown in FIGS. 5b and 5c, a base tone 38 can be output to both ears 32 and 33. This base tone 38 can be a very low-volume tone. The permanent, low-volume base tone serves to be able to perceive the generated tone differences more sensitively. Moreover, the base tone 38 is a kind of control tone. If this is no longer output, the user can conclude that the procedure has malfunctioned or has been interrupted.

According to the method shown in FIG. 5b, the position/inclination of the body is not to be corrected if only the base tone 38 is output. If the tone in one ear, in this case the left ear 32, changes, for example in terms of volume, modulation or certain sound effects, the position of the body must be corrected. Based on the stereo acoustic signal output in the left ear 32, the user is informed that his body is inclined to the left and that a corresponding correction movement must be made to the right.

FIG. 5c shows another possibility with regard to the conversion of the body position data into an acoustic signal. This embodiment of the conversion can be called a stereo switching method. If an equivalent stereo signal is heard in both ears 32 and 33, i.e. in equal proportions in the left and right ear, the body position or inclination of the body does not have to be corrected. If the acoustic signal increases on one side, i.e. in one ear, and if at the same time the acoustic signal is reduced equally on the other ear, the position of the body must be corrected accordingly. In the example shown, the tone in the left ear 32 increases from 50% by 40% to 90%. And in the right ear 33, the acoustic signal is reduced from 50% to 10%. This means that there is an inclination to the left and the body position must be corrected accordingly to the right.

Figure 5D:
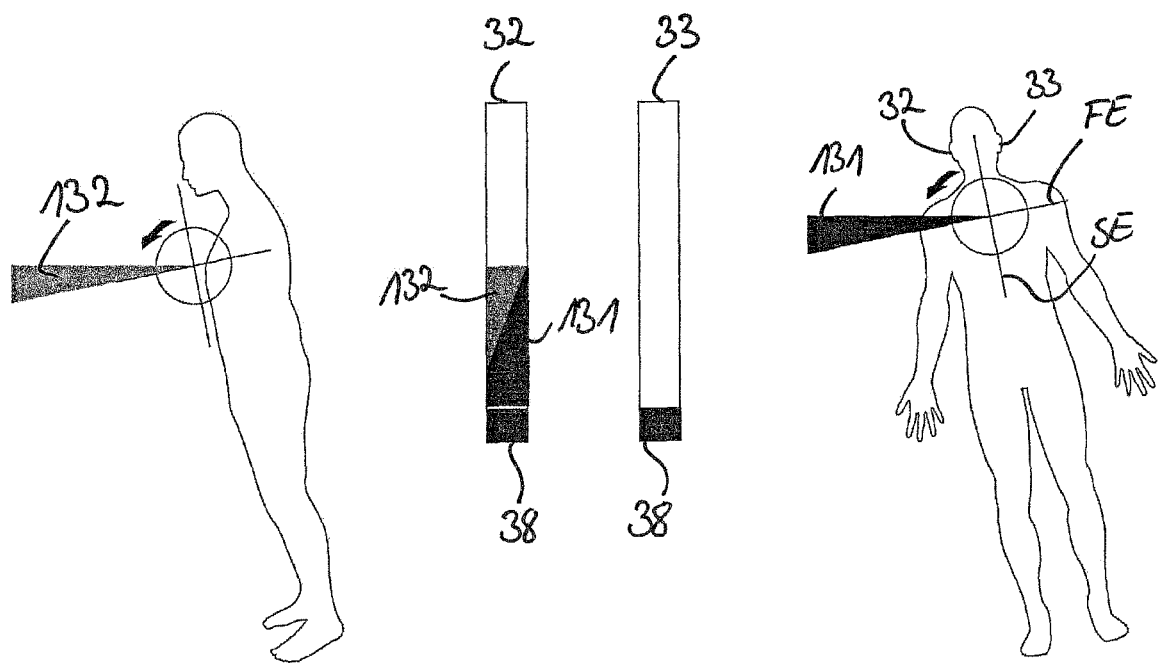

FIG. 5d also indicates that the inclination in the sagittal plane is also taken into account when converting the body position data into at least one acoustic signal. A first acoustic signal 131 is shown. This acoustic signal 131 is associated with a deviation from the 0° position of the body to the left or to the right.

It is also indicated that a second acoustic signal 132 is generated in connection with the deviation from the 0° position of the body forwards or backwards. In other words, a second acoustic signal 132, in particular a second stereo acoustic signal, is added in case of a forward or backward inclination. In the case of a forward or backward inclination, this second stereo acoustic signal 132 increasingly replaces the first stereo acoustic signal 131 (cross-fade), depending on the magnitude of the inclination and predefined settings. However, at the same time, the second acoustic signal 132 at the same time permanently conforms to the left-right ratio of the first acoustic signal 131.

As shown in connection with the left ear 32, the second acoustic signal 132 mixes with the first acoustic signal 131 depending on the degree of inclination. This is done up to the maximum drowning of the first acoustic signal 131.

Figure 5E:
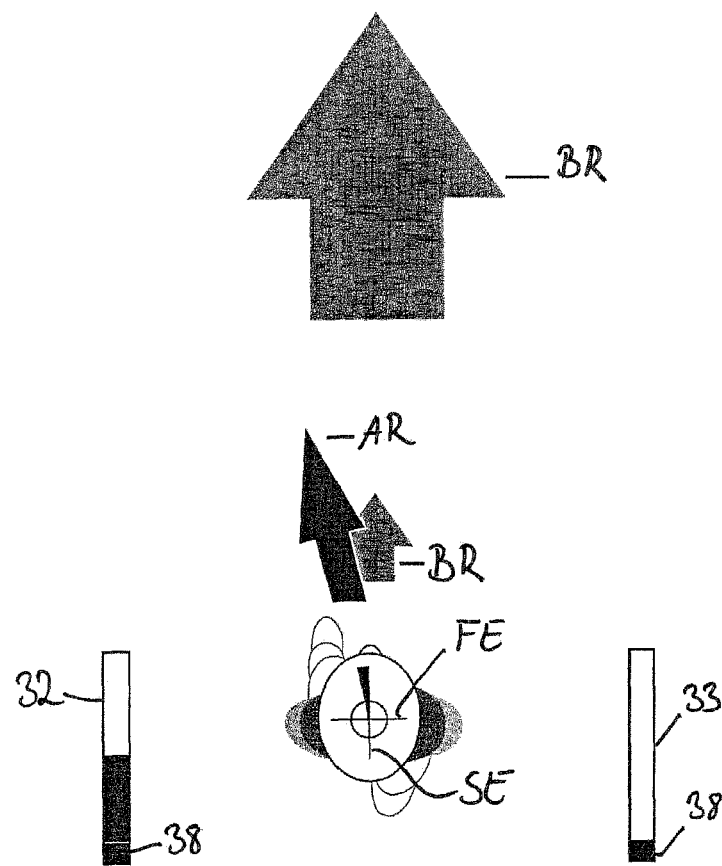

FIG. 5e shows that in step a) the average direction of movement BR of the body 10 and a deviation AR from the average direction of movement are determined. This data regarding the deviation AR from the average direction of movement BR can also be used in step c), i.e. when converting the body position data into at least one acoustic signal. Here, the direction of movement must first be detected in a process step. If the average direction of movement BR has been determined, a deviation AR from this direction of movement BR can be detected or determined.

In the example shown, the deviation AR is signaled by an acoustic signal in the left ear 32. Thus, deviations from a straight gait can also be detected and signaled. An inclination in the upper body of the user or the body 10 is not necessary here. A gait pattern that shows a sway is not generally associated with a leaning or inclined body. Rather, a swaying tendency can result from side steps or balancing steps. Due to the inclusion of deviation AR from the direction of movement BR during the conversion of the body position data into at least one acoustic signal, an advanced gait pattern improvement can be provided.

The conversion of the data regarding the deviation AR into an acoustic signal can be carried out as already described in connection with a body inclination to the left or right (or forwards or backwards). For example, if a threshold value, which can also be called a minimum value, is exceeded, an acoustic signal, in particular an increasing acoustic signal, can be output in the left ear to indicate a deviation from the direction of movement to the left. A deviation AR from the average direction of movement BR may be detected, for example, by determining a difference between the average direction of movement BR and the upper body alignment.

Furthermore, in FIG. 5e, the previously mentioned planes are marked, namely the sagittal plane SE and the frontal plane FE.

In FIG. 6, individual components or component groups of the inventive system are shown.

First, a body position sensor unit 45 is shown. This body position sensor unit 45 can comprise position sensors 40, which are formed separately from a mobile communication device. Furthermore, these can be sensors integrated into a smartphone 20. In particular, these can be position sensors, gyro sensors, gravitational sensors, acceleration sensors, tremor sensors, rotation sensors, magnetic sensors as well as mechanical sensors such as a cable sensor.

Furthermore, an external sensor unit 25 can be formed alternatively or additionally. This can be a camera, in particular a Kinect camera, i.e. a camera with depth sensors, or a balancing board. The body position data recorded by the body position sensor unit 45 are then sent as sensor data SD to the arithmetic unit 55. The arithmetic unit 55 can be part of a controller unit 56. Furthermore, the controller unit can comprise a storage 57. For example, a selection of system parameters can be stored in storage 57. The values n1 and n2 can also be stored there. It is also possible to store the selection of the sound method, logarithms, volume ranges, etc. in storage 57.

Furthermore, the controller unit 56 can have a communication unit 58. This communication unit 58 serves as an interface for data transmission. In this context, data can be exported as well as imported. The communication unit 58 can be a USB interface as well as a radio interface. Furthermore, with the help of the communication unit 58, Internet access can be provided via UMTS/LTE or WiFi. Furthermore, the communication unit 58 can comprise an interface to an online database.

Furthermore, an input and output module 130 can be formed. This can comprise a display unit 110 as well as a control unit 120. As already explained in connection with FIG. 3*d*, threshold values relating to the detected sensor data SD can be determined with the help of control unit 120. The display unit 110 serves, for example, for displaying graphs 101 as well as active ranges 102. Therefore, video signals VD can be sent to the display unit 110.

An audio module 35 is also shown. This audio module 35 can comprise the previously described audio mixer unit 36 as well as the sound generation unit 37. Audio module 35 serves to generate audio data AD, i.e. acoustic signals which are sent to an output unit 140 for outputting an acoustic signal. In other words, sound generation unit 37 is an audio source for the generation of sound. This can be a tone generator or a synthesizer. An audio player can also act as a sound generation unit 37.

Furthermore, audio module 35 can have an audio signal input 39*b* as well as an audio signal output 39*a*. An audio signal input 39*b* is required if the audio module 35 has a sound generation unit 37. The audio signal input 39*b* can be designed as a socket for wired audio reception and as a wireless receiver, e.g. as a BLUETOOTH short-range wireless communication technology standard interface. The audio signal output 39*a* is the interface of the audio module 35, which sends the audio signal or the audio data AD to the output unit for outputting the acoustic signal 140. This can be a socket for wired audio output as well as a transmitter for wireless audio output, e.g. a BLUETOOTH short-range wireless communication technology standard interface.

The modules, units, and components shown in FIG. 6 can also be formed independently of one another and in any possible combination in an embodiment of the inventive system.

FIG. 7*a* shows a secure platform with database 90 for analysis data that can be viewed by researchers, doctors 80, therapists and patients. Thus, a connection can be established from the system to a database 90 and from the database 90 to a doctor 80. Preferably, the platform with database 90 is an online platform.

FIG. 7*b* additionally shows a monitoring unit 160. The monitoring unit 160 may be a second wireless interface device running in parallel, in particular a mobile communication device that is connected to the user's system. The monitoring unit 160 serves to enable persons such as doctors and trainers to monitor, but also to intervene in real time if necessary.

This corresponds more or less to a remote function. As regards a remote function, the following is stated: Real-time remote access to the user is facilitated for therapists in order to be able to observe and analyze the processes on site during gait tests, but also by means of remote analysis, and optionally make modifications or adjustments to the app/method.

In addition, reference is made to other embodiments and/or advantages obtained with the inventive system and/or the inventive method and/or the inventive computer readable storage medium:

Interfaces and data connectivity: The app/method is provided for uncomplicated expandability and programming of interfaces for existing databases. This way, the analysis values of the patients can be transmitted after an interface has been programmed.

External devices: As an alternative or in addition to the app/the computer readable storage medium, stand-alone sensor and feedback devices, in particular external mobile communication devices, can be provided, which optimize wearing comfort, battery life, measurement accuracy and are connected at appropriate intervals to a smartphone or mobile communication device and store and transmit the measurement data.

This allows the modular selection of how an output unit for outputting an acoustic signal and an output unit for outputting a vibration signal are combined. The devices communicate independently with one another.

App for external device: An extra app can be formed for the external apparatuses. It connects via radio signal, especially via BLUETOOTH short-range wireless communication technology standard, to the external/autonomous devices, adjusts them, collects data, and makes them accessible online.

Accessories: Carrying devices are provided, in particular pouches/pockets and/or garments, which optimize the wearing comfort and design. FIG. 2*b*, for example, shows that carrying device 60 can be formed as a long-sleeved shirt, close-fitting to body 10, whereby the carrying device 60 has at least one pocket 61.

Sound development: Especially for the respective needs, therapy goals and psychological findings, sounds/tones are provided, which are added to the app/a storage/a program and are preferably available online.

The target groups of the inventive method or the inventive device are, for example, patients with balance disorders. The supplementation of the disturbed sense of balance by means of additional sensors, in particular by means of additional position sensors, particularly preferably by means of a body position sensor unit, and by reliable, permanent and fast-to-process feedback in the ear and on the body, creates a feeling of safety.

Steady self-confidence of the patient with balance disorders can be achieved. Through the repeated use of feedback and acoustic signaling, respectively, this stimulation achieves a new sensitization of one's own body position and also a learned, sustainable body stabilization.

The inventive system and the inventive method, respectively, comprise safety and control aspects for doctors, therapists and patients in walking or movement therapies. It is possible to correct and individually analyze and support persons with walking disorders, posture disorders and patients after pelvic and knee operations in training or rehabilitation phases. A recording function with an online database enables patients in therapy phases, medication and treatment to be analyzed regularly and individually and to be treated in an optimized fashion.

The inventive system and the inventive method, respectively, also offer benefits to researchers, analysts, physicians, and therapists. Measurements can be carried out on test persons for analyses with convenient progress monitoring for new treatment methods, therapy sets, and drugs. Athletes and coaches can also benefit from the inventive method and the inventive device, respectively. In order to optimize the training, measurements can be performed by means of the method, the computer readable storage medium, the app or the system. These measurements can also be performed after operations or accidents.

At this point, it should be noted that all the parts described above are considered to be individual and are claimed to be essential to the invention in every combination, in particular the details depicted in the drawings. Modifications thereof are familiar to those of ordinary skill in the art.

LIST OF REFERENCE NUMERALS 10 body
20 smartphone
25 external sensor unit
30 stereo acoustic signal
31 headphones
32 left ear
33 right ear
35 audio module
36 audio mixer unit
37 sound generation unit
38 base tone
39a audio signal output
39b audio signal input
40 position sensor
45 body position sensor unit
50 vibration signal
55 arithmetic unit
56 controller unit
57 storage
58 communication unit
60 carrying device
61 pocket
70 carrying device
71 pouch
72 chest strap
73 shoulder strap
80 doctor
90 platform
100 representation
101 graph
102 active range
110 display unit
120 control unit
130 input and output module
131 first acoustic signal
132 second acoustic signal
140 output unit for outputting an acoustic signal
150 output unit for outputting a vibration signal
160 monitoring unit
201 to 203 process steps
AD audio data
AR deviation from direction of movement
BR direction of movement
FE frontal plane
N inclination
n1 first sensor value
n2 second sensor value
SD sensor data
SE sagittal plane
StS control signal
VD video data

SEQUENCE LISTING

Not Applicable

What is claimed is:

1. A method for posture and movement regulation for humans using a system for posture and movement regulation, the system comprising at least one body position sensor unit (45), at least one arithmetic unit (55), and at least one acoustic output unit (140) for outputting at least one stereo acoustic signal to a user having a body, a right ear and a left ear, wherein the at least one stereo acoustic signal comprises at least a first channel signal and at least a second channel signal, the first channel signal and the second channel signal being independent from one another, wherein the first channel signal is output to the left ear of the user and the second channel signal is output to the right ear of the user, wherein the output of the first channel signal and the second channel signal to the respective ears of the user is indicative of at least a first body position state and a second body position state, and wherein the first body position state is different from the second body position state, the method comprising the steps of:
   a) determining the body position data of the human body (10) including collecting data regarding a step force via a tremor sensor,
   b) sending the body position data to the at least one arithmetic unit (55),
   c) converting the body position data into the at least one stereo acoustic signal,
   d) sending the at least one stereo acoustic signal to the at least one acoustic output unit (140) for outputting the at least one stereo acoustic signal.

2. The method of claim 1,
characterized in that
in step c), a comparison of the body position data with target body position data is performed.

3. The method of claim 1,
characterized in that
prior to step a), a calibration step is performed, in which the 0° position of the human body (10) is determined.

4. The method of claim 1,
characterized in that
in step a), the body position data are determined in the sagittal plane (SE) and in the frontal plane (FE) of the body (10).

5. The method of claim 4,
characterized in that
the at least one stereo acoustic signal includes a first stereo acoustic signal and a second stereo acoustic signal, and
in step c), the first stereo acoustic signal (131) is generated for the body position data in the frontal plane (FE) and the second stereo acoustic signal (132) is generated for the body position data in the sagittal plane (SE).

6. The method of claim 1,
characterized in that
in step a) the average direction of movement (BR) of the body (10) and a deviation (AR) from the average direction of movement are determined.

7. The method of claim 1,
characterized in that
the body position data is stored and/or the body position data is sent to a database (90).

8. The method of claim 1,
characterized in that
the body position data determined in step a) is converted into a visual image (100, 101) and sent to a display unit (110) and/or stored in a database (90).

9. A non-transitory computer readable storage medium containing instructions that cause at least one processor to implement the method of claim 1 when the instructions are executed by the processor.

* * * * *